(12) United States Patent
Skupin (10) Patent No.: US 9,934,359 B2
(45) Date of Patent: Apr. 3, 2018

(54) DEVICE AND METHOD FOR THE CENTRAL CONTROL OF DEVICES USED DURING AN OPERATION

(75) Inventor: Horst Skupin, Villingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1684 days.

(21) Appl. No.: 12/126,584

(22) Filed: May 23, 2008

(65) Prior Publication Data

US 2008/0294458 A1  Nov. 27, 2008

Related U.S. Application Data (60) Provisional application No. 60/945,442, filed on Jun. 21, 2007.

(30) Foreign Application Priority Data

May 25, 2007  (EP) ..................................... 07010474

(51) Int. Cl.
  *G06Q 50/22*  (2018.01)
  *G06F 19/00*  (2018.01)

(52) U.S. Cl.
  CPC ......... *G06F 19/3406* (2013.01); *G06Q 50/22* (2013.01)

(58) Field of Classification Search
  None
  See application file for complete search history.

(56) References Cited

U.S. PATENT DOCUMENTS 5,157,603 A * 10/1992 Scheller ................. A61B 17/32
                                                              604/22
5,788,688 A *  8/1998 Bauer .................... A61B 90/36
                                                              606/1

(Continued)

FOREIGN PATENT DOCUMENTS

DE   9218373 U1   1/1994
DE  19904090 A1   8/2000

(Continued)

OTHER PUBLICATIONS

European Search Report, EP07010474, dated Nov. 21, 2007, 3 pages.

(Continued)

*Primary Examiner* — Neal Sereboff
(74) *Attorney, Agent, or Firm* — Whitmyer IP Group LLC (57) ABSTRACT

To be able to use a generally available database of predetermined apparatus configurations and parameters in medical interventions, a device is disclosed for controlling and/or monitoring at least one apparatus during a medical intervention, said device including a least one control unit for controlling and/or monitoring the at least one apparatus and at least one display unit for displaying data, wherein: access is possible to data specific to the intervention, including at least data on the parameter values to be entered on the at least one apparatus during a predetermined intervention; in addition the parameter values are predetermined at least in part depending on the user, while the parameter values can be called up by a user for display by means of the display unit, and a confirming element is provided, through whose actuation the predetermined parameter values for the at least one apparatus are incorporated.

18 Claims, 1 Drawing Sheet

(56) References Cited

U.S. PATENT DOCUMENTS

| | | | |
|---|---|---|---|
| 5,819,229 A | 10/1998 | Boppe | |
| 6,086,544 A * | 7/2000 | Hibner | A61B 10/0275 |
| | | | 600/564 |
| 6,397,286 B1 | 5/2002 | Chatenever et al. | |
| 6,708,184 B2 | 3/2004 | Smith et al. | |
| 6,928,490 B1 | 8/2005 | Bucholz et al. | |
| 7,525,554 B2 * | 4/2009 | Morita | G06Q 50/22 |
| | | | 345/619 |
| 2002/0112525 A1 * | 8/2002 | Brockhaus | 73/1.16 |
| 2004/0030367 A1 * | 2/2004 | Yamaki | A61B 1/0005 |
| | | | 607/60 |

FOREIGN PATENT DOCUMENTS

| | | |
|---|---|---|
| DE | 102004046430 A1 | 4/2006 |
| DE | 69734592 T2 | 8/2006 |
| EP | 1034480 B1 | 12/2005 |
| EP | 1770569 A1 | 4/2007 |
| WO | 0219957 A2 | 3/2002 |

OTHER PUBLICATIONS

Storz Advertising Literature—Karl Storz OR1tm—Recommended Configurations, ENDOWORLD OR1-10-2-E, Nov. 2005, 12 pages.

* cited by examiner

DEVICE AND METHOD FOR THE CENTRAL CONTROL OF DEVICES USED DURING AN OPERATION

CROSS-REFERENCE TO RELATED APPLICATIONS

The present application claims priority of European patent application No. 07 010 474.0 filed on May 25, 2007. The present application also claims the benefit under 35 U.S.C. § 119(e) of the U.S. Provisional Patent Application Ser. No. 60/945,442 filed on Jun. 21, 2007. All prior applications are herein incorporated by reference in their entirety.

FIELD OF THE INVENTION

The present invention relates to a device and a process for central monitoring and/or control of at least one apparatus, which is used during a medical intervention, having at least one control unit for controlling and/or monitoring the at least one apparatus and having at least one display unit for displaying data, where access is possible to data specific to the invention, said data including at least data on parameter values to be adjusted on the at least one apparatus in a given intervention.

BACKGROUND OF THE INVENTION

With the increase in the number and complexity of the apparatuses that are coming into use in medical interventions of all types, especially in minimally invasive surgical operations as well as in diagnostic or non-invasive therapeutic procedures, there also come growing demands on the handling by the responsible physician. Therefore, to facilitate such handling, to increase security, and to improve documentation and administrative processes, by means of one or more control units, systems have been created in which a number of medical and non-medical apparatuses that are used in an operation can be handled.

Such installations for central monitoring and/or controlling apparatuses coming into use during an operation are known, for instance, from the publications DE 92 18 373 U1, EP 1 034 480 B1, or WO 02/19957, to which express reference is made for elucidating all details not described in greater detail here. DE 199 04 090 A1 discloses the connection of individual apparatuses and a master computer to one another by a CAN-bus, so that the individual apparatuses serve as slaves and the master computer as master; all apparatuses can be controlled by the master computer.

Because the functioning of the apparatuses being used is determined by various parameters, such as for instance insufflation pressure, high voltage current, and so on, it is foreseen that these parameters can be entered by means of an entry unit, such as a touch screen; also known in the art is the fact that apparatus parameters entered by the physician are stored in a memory device and can be called up from it for use in a later operation. Such a system for control of installations that are used in a surgical operation is proposed for instance by the KARL STORZ firm under the designation "OR1®" (see www.karlstorz.de).

The publications U.S. Pat. No. 6,708,184 and U.S. Pat. No. 6,928,490 teach means of making information from the Internet available for the physician during the operation, such as a digital anatomical atlas. Likewise, U.S. Pat. No. 5,819,229 discloses the use of databases in the context of an integrated operation assistance and monitoring system, said databases being used for archiving patient information and for registration of parameters arising during the operation. Information stored in the databases, however, cannot be used for direct control of the medical apparatuses that are used during the surgical intervention.

DE 697 34 592 T2 discloses a system for controlling ophthalmologic surgical interventions that comprises surgical modules connected with microsurgical instruments, a data transmission bus, and a user interface. The user interface contains a processing device and a storage device for storing a number of apparatus parameters for the microsurgical instruments. By means of the processing device a group of parameters can be called up and transmitted by the data transmission bus to the surgical modules that control the microsurgical instruments, depending on the group of parameters called up from the storage device. The user interface comprises a menu in which the particular attending surgeon, for instance under his own name in a surgeon selection menu, can combine the apparatus parameters of the microsurgical instruments into separate groups that he considers advantageous for conducting a specific surgical intervention. These separate groups of parameters are filed in submenus to the master surgeon selection menu and are accordingly selected by the surgeon for conducting a particular operation. The publications U.S. Pat. No. 5,788,688 and U.S. Pat. No. 6,397,286 also teach that the surgeon, depending on the situation, can call up and use preferred apparatus configurations that have been previously defined for particular interventions and stored in a medical control system.

The disadvantage here is that the surgeon for a particular surgical procedure cannot resort to parameter values available in the system and apparatus configurations that have proven themselves in a number of surgical interventions of the same type. Instead, he himself must assemble the apparatuses required in a particular medical intervention and must implement the optimal parameter settings for them in the system in order to be able to have access to them in a concrete situation. This, however, is time-consuming and potentially error-prone, because it is not possible for every physician and every clinic to have the necessary experience to ascertain the optimal configurations and parameter values for all types of interventions and for all situations arising in practice.

It would thus be desirable to be able to utilize a widely available database of predetermined configurations and parameters of apparatuses that are independent of the particular physician and shown to be optimal in a number of operations and established by recognized specialists. On the other hand, such predetermined parameter values may not be the optimal ones for every individual case or for every patient. Therefore it is essential for safety reasons that the particular physician who is operating should, before the operation, become fully aware of the apparatus parameters that are to be entered and should accept them with a view to the concrete situation. However, it is impossible to exclude any possibility of neglecting this awareness in the midst of constantly recurring routine interventions or even in emergency and stress situations which always arise in operations.

It is therefore the object of the present invention to provide a system and a process for controlling and/or monitoring apparatuses in medical interventions, where in such a system or process, on the one hand, access is possible to generally valid apparatus configurations and parameters that are proved to be optimal in a number of comparable interventions, while on the other hand there is an assurance that the physician has taken positive note of them in every intervention.

SUMMARY OF THE INVENTION

This object is fulfilled with a device and process according to the invention.

Because access is provided to predetermined parameter values, which are not entered by the particular user, for the apparatuses used in a particular type of operation, and because at least one confirming element is provided whose actuation is necessary for incorporating the predetermined parameter values by the apparatuses, it is guaranteed that the responsible physician on the one hand can have recourse to predetermined, generally valid parameters that have been proved in a number of comparable operations, but at the same time is compelled to be aware of them. The parameters that have been called up by the attending physician are indicated to him by means of the display unit for purposes of evaluation and release. The confirming element requires active actuation by the physician as the responsible user of the system and thus forces him to make a deliberate confirmation of the parameter values that are to be taken over.

The confirming element leaves the attending physician the choice between approving the selected parameter settings, resulting in the release of the parameters or the incorporation of the parameter values by the apparatuses, and rejecting the settings. To accomplish this, the following question, for instance, is addressed to the attending physician by the output device of the system: "Do you consent to the selected parameter values?" The attending physician, through corresponding actuation of the confirming element, can then answer the question in the affirmative or the negative. The attending physician is therefore forced to be conscious of how suitable the parameter settings incorporated from the database are to the conduct of the specific intervention on the particular patient.

In addition, according to a preferred embodiment of the invention, the physician has the possibility of modifying the values of individual parameters that are depicted by the display unit and then to consent to the totality of the parameter settings, partly modified and partly unchanged, by actuating the confirming element, thus triggering the release of the parameters or the incorporation of the values of the selected parameters by the apparatuses being used. This has the advantage that the physician is not forced to incorporate the predetermined parameters unchanged, but instead can adjust them according to his/her judgment to the particular situation and/or to the specific patient. Thus, for instance, operations on children, adipose patients, or patients belonging to particular risk groups require specific adaptation of the apparatus configurations and parameter values.

Moreover, because the type and number of the apparatuses required in a particular intervention are subject to generally valid considerations, it is provided in an additional preferred embodiment that the predetermined data specific to an intervention can also include predetermined data about the apparatus configuration to be used in the foreseen intervention. This ensures in every case that the combination of apparatuses that is optimal for the particular intervention is proposed to the attending physician, and for at least some of these apparatuses the predetermined parameter values are also displayed and that the physician can release or modify them.

According to another preferred embodiment of the invention, the predetermined parameter values, possibly modified by the user, after actuation of the confirming element are transmitted to the apparatus or apparatuses that are used in the intervention and that then incorporate the particular setting. This can occur, for instance, through a bus system basically known in the art and constitutes a simple and secure solution.

As an alternative to this, the predetermined and possibly modified parameter values could be transmitted to the apparatuses to be used in the intervention even before the actuation of the confirming element, for instance after the predetermined parameters are called up by the user or simultaneously with the display of the predetermined parameters on the display unit, or with a modification by the user. After actuation of the confirming element, there remains only one more activation signal to be transmitted, which causes the incorporation of the already transmitted data. This mode of operation is advantageous if, for instance, greater data volume is to be transmitted or the incorporation of the parameters by the connected devices requires more time.

In both cases the connected apparatuses can immediately execute the action determined by the transmitted parameters, such as for instance the creation of a particular light capacity, high voltage current, or a particular pressure, or it can merely be placed in readiness for this, so that the action is triggered only by an additional signal, possibly one automatically created by a sensor.

According to an additional preferred embodiment, actuation of the confirming element triggers storage of the selected and released apparatus configuration and apparatus parameters. This consequently fulfills the requirements for comprehensive documentation in connection with surgical interventions. As a result, it is also possible to open an electronic patient data file for containing data that arise subsequently on the operation of the employed apparatuses, as well as, for instance, image data from the operation. At the same time additional actions can be triggered, such as the entry of a corresponding text module into an OP report form or reordering working materials.

In another preferred embodiment, the confirming element is configured as a switch, for instance as a pushbutton, tip switch, slide switch, or lock with releasing key or the like, so that a control element is provided that, upon actuation of the confirming element, emits a detectable signal such as a control lamp that lights up, or an acoustical element that produces a control tone. This has the advantage of being especially cost-effective and easy to produce and in the process offers a high degree of security and reliability.

In addition, for reasons of security or documentation, authentication of the physician may be demanded, for instance by means of a key, password, barcode, magnetic card, a chip that is also automatically readable, biometrical data such as fingerprint or interocular distance, or some other means of individually identifying the physician. This measure ensures that the confirming element is actuated only by a person known and qualified to the system.

In an especially preferred embodiment the confirming element is configured as a switch surface, for instance with selection buttons, on the operating surface of a touch screen that can serve at the same time as an output device of the parameter settings for controlling the apparatuses. If it is foreseen that the physician can modify the parameters before they are incorporated by the apparatuses, the values of the parameters can be modified, for instance by sliding switches or pushbuttons on the operating surface of the touch screen. This embodiment allows for especially simple, comfortable, and clearly visible operation of the entire system, so that its general operational safety is also increased.

To increase security, a first confirming element can also be provided which serves for selecting individual predetermined or modified parameter values, and a second confirming element that can be actuated with the first confirming element only after selection and approval of the parameter settings. Only actuation of the second confirming element allows the user to operate the apparatuses with the parameter settings previously selected by the first confirming element. By actuating the second confirming element, the parameter values are finally released and the system is made "sharp," so to speak. This measure increases the system's security and avoids accidental operation of the security-relevant apparatuses with inappropriate or even wrong parameter settings.

In another preferred embodiment a first confirming element is foreseen for selecting settings and parameters for controlling non-security-relevant apparatuses and a second confirming element for selecting settings and parameters for controlling security-relevant apparatuses.

According to an especially preferred embodiment of the invention, the predetermined apparatus configurations and parameters are part of a database. This database can be, in particular, an OP atlas or an OP knowledge base, which can contain a number of other data, in particular lexical data, image data, instructions specific to individual interventions with indications of the individual operations steps and warning signals for the attending physician, indication of the instruments and apparatuses to be used and their settings, and so on. This information, which is also contained in part in the printed form of an OP atlas, is filed in the database in digitized form and can be called up by the physician in the operating room and shown on the display unit in order to provide the physician with information essential for the particular intervention.

Thanks to this form of database, the physician has access to parameter settings for controlling the security-relevant apparatuses that are adapted and optimized for the particular medical intervention. In addition the physician has recourse to the other information contained in the digitized OP atlas.

The database can be structured in such a way that the user can access data relevant for the particular intervention by entering application-specific key words or by means of a menu control that displays applications that are constantly more precisely specified by area of specialty and in steps. In calling up the image or text data that belong to a particular intervention, the relevant apparatus configurations and parameters can then be depicted and offered for confirmation by the confirming element.

The database can have a browser available for navigating among various specialized areas and subfields in the database. A navigation concerning the operative access routes can also be produced which, for instance can be further broken down by specialized area and intervention. The choice of the operative access route determines, for instance, the requirements on lighting arrangements in the operating room and the spatial situation, orientation, and positioning of the operating table. The corresponding configurations and parameter setting can be combined and called up depending on the access routes. By actuating a first confirming element, a particular access route can then be selected. This makes possible easy switching between various operating access routes, for instance between vaginal or laparoscopic access. In the further navigation of the database, the apparatus configurations and parameter settings for controlling the apparatuses, which are necessary for performing the specific intervention, are selected by actuation of a second confirming element.

Even optimized apparatus configurations and parameter settings that are filed in such a database may not be optimal for all situations arising in reality, which can arise acutely during an intervention or can be related to the patient's anatomical characteristics. Resulting departures from the predetermined sequence cannot all be anticipated by the producer of a database. It is the task of the attending physician to react appropriately to them, particularly in planning, preparing, and performing the medical intervention.

It is possible, however, at least partly to foresee some system- and situation-dependent influences on the necessary configurations and parameter settings. Just as the apparatus configurations and optimal parameter values can vary depending on the producer and model of the apparatuses employed, so too the patient data, such as age, size, weight, existing or previous known illnesses and anatomical particularities, can require modified parameter values.

To the extent that these system- and situation-dependent influences can have a foreseeable impact on the optimal apparatus configurations and parameter settings, they can be taken into account in the predetermined data, for instance in the database. Thus the database, for instance, can contain various sets of parameters for various producers or models of the apparatuses that are to be used. In a preferred embodiment of the invention, on calling up the data specific to the intervention, it is possible to display the particular data set that corresponds to the apparatuses in actual use. The data required for this are stored in the inventive device, or they can be accessed by calling up the data specific to the intervention. It is likewise possible to store various data sets depending on patient data and to call up the one that corresponds to the patient data available in the OP control or in a connected network. Alternatively, rather than storing for instance an individual set of apparatus parameters for every possible combination of patient-specific data, a formula can be entered for calculating patient-dependent parameters, from which the displayed parameter values that are to be incorporated are ascertained with the help of the available patent data, for instance also by interpolation or extrapolation from predetermined benchmarks.

In a preferred embodiment of the invention, the database, with the parameter settings for controlling the apparatuses, is installed in the storage unit of an external server to which the inventive device can gain access, for instance over a local network or the Internet.

Thanks to this measure, the database, with the parameter settings for controlling the apparatuses, can be especially easily processed and updated and at the same time made available to a number of users, who can gain access to the parameter settings from various operating rooms inside a clinic or from various clinical locations around the world. Thus the optimization of the performance of medical interventions is facilitated and a contribution is made to their quality assurance.

In another preferred embodiment of the invention, the database of the parameter settings for controlling the apparatuses is installed on a control unit of the system and is filed in the storage facility of the control unit. Thanks to this measure, the need for additional apparatuses such as scanning devices is kept low and thereby the equipment dysfunction risk for the system is reduced, for a gain in equipment security.

In an additional preferred embodiment of the invention, the storage facility is configured with the database of the parameter settings for controlling the apparatuses as a purely readable data carrier, for instance as a read-only CD, CD-ROM, or DVD. A control unit can have access to the parameter settings that are found on the read-only data carriers by means of a corresponding reading device such as a CD, CD-ROM, or DVD drive. This embodiment ensures flexible operation. The system can gain access to improved and processed parameter settings especially easily in the form of updated versions of the databases on read-only data carriers. Thus the database can be a component of the software of the control unit or of the bus system, and thereby can be updated along with each updating of the operating software.

In an additional preferred embodiment of the invention, the confirming element serves only to confirm the parameter values of some of the apparatuses used in the particular intervention, in particular that of the security-relevant apparatuses. Consequently the physician is relieved of having to review data that are less relevant for the patient's security.

In an additional preferred embodiment of the invention, the control unit is installed in such a way that before release of the parameter values, plausibility tests are undertaken at least for controlling security-relevant devices. If a group of parameter settings for performing a specific procedure is selected from the database, then these parameter settings are subjected to plausibility tests that are performed by routines that are implemented on a control unit. For example, keystrokes cannot assume negative values, so that a review of the prefix sign of the numerical value can shed light on the parameter setting. The values of parameter settings from databases can include errors, which can arise in populating large data amounts by faulty transmission of the values. If the selected parameter settings prove in a plausibility test to be faulty, then a new selection of parameter settings must ensue or the faulty value must be corrected by entering a correct value by means of an entry device. Conducting plausibility tests on parameter values constitutes a measure that advantageously raises the security of the system and facilitates operation of the system.

Similarly, the control unit can be set up in such a way that before release of the parameter values, plausibility tests are conducted to verify for apparatus or operating errors. If, for instance, an apparatus is not yet connected to the power supply or if a high voltage cable is faulty, this can automatically be recognized and indicated before release of the parameter values or the release of the parameter values can be refused. Likewise, during the operation of the apparatuses such a test can take place and the result can be displayed, possibly with a warning signal.

In another embodiment, a dynamic adaptation of the apparatus configurations and parameter settings to the current requirements can take place during the intervention. Vital parameters such as blood pressure, breathing frequency, heartbeat, pulse, oxygen content of the blood, or the bodily temperature can be taken on the patient during the medical intervention and can be compared with recorded target values or target ranges. If the value readings depart from the target values or ranges, then it is possible by means of the control unit of the at least one apparatus to calculate new apparatus configurations and parameter settings, which are displayed on the at least one display unit. By actuating the confirming element, the physician can approve these apparatus configurations and parameter settings that are adapted to the situation.

In addition to the vital parameters, it is also possible to use measured data, which are registered for instance by the apparatuses that are to be controlled, for dynamic adaptation. Here reference can be made to the information of an OP atlas or an OP knowledge base. This information together with the captured measured values can be calculated by appropriate algorithms and simulations to determine adjusted apparatus configurations and parameter settings.

In all cases, however, the attending physician or an authorized person taking part in the medical intervention must give approval to the dynamically adapted apparatus configurations and parameter settings by actuating the confirming element.

An additional preferred embodiment foresees an at least partly telemedical remote control of the inventive device. Here the at least one confirming element is configured in such a way that every actuation of the confirming element includes a check of the identity of the person who is actuating and the transmission of the confirmed apparatus configurations and parameter settings takes place only upon positive authentication of the actuator.

This measure has the advantage that specialized physicians at a distance can not only take part in the medical intervention as consultants, but can exert an immediate influence on the medical intervention.

It is often desirable for ergonomic reasons to be able to conduct remote control or operation of all systems needed during an operation from a central location, if possible from the sterile area. Such control can take place, for instance, by way of a touch screen (with sterile covering) or with speech control. Controlled devices or systems can include, for instance, endoscopic apparatuses such as OP table, OP lighting, anaesthetic units, devices for monitoring the patient's condition, respirators, room lighting, air conditioning, telephone, pager, Internet, hospital information system, disposable materials, administrative system, and others. All can be controlled by a single control unit, so that the individual apparatuses are connected by way of a CAN bus for instance and the control unit operate as master and the apparatuses as slaves.

The disadvantage of such a networking consists in particular in the fact that the software and hardware complexity for the individual control unit is very high, because it must be adapted to the device that is to be controlled with the highest security requirements. With apparatuses that are to be controlled that do not need to meet such high security requirements, flexibility or simplicity of operation can possibly be lost. However, if the individual control unit has been constructed with a view to security aspects according to less stringent standards, then there could be a risk (for instance with a PC with standard software) that security-relevant functions are endangered by unreliable functions of the non-security-relevant systems.

Apparatuses used in a medical intervention, particularly in a surgical operation, can be divided into two distinct groups: on the one hand, security-relevant devices such as endoscopic light sources, insufflators, irrigation and suction pumps, high voltage generators, OP table control, etc., that is, devices in which an outage or error could be life-endangering for the patient, and on the other hand non-security-relevant as well as non-medical devices such as jalousies, image archiving, room lighting, telephone, air conditioning, pagers, Internet, material administration, etc.

In an especially preferred embodiment of the invention, a second control unit is therefore foreseen which is connected with the first control unit for data exchange. The first control unit is configured as a closed system for control of at least those devices that fill security-relevant functions, a system that cannot be configured by the user, while the second control unit is configured as an open system for controlling the other apparatuses.

This increases security with respect to undesired dysfunctions without thereby restricting the flexibility of the entire system. Because on the second control unit, for instance, it is also possible for software to come into use that is not required to fulfill the strict security criteria for control of security-relevant devices, it is possible to make use of more economical standard software.

Because the first control unit, which is responsible for the control of the security-relevant devices, is configured as a closed system, there is assurance that no manipulations of the operating system or of the applications for controlling the security-relevant devices are possible. In addition, on the first control unit it is possible to run applications for controlling non-security-relevant devices provided such applications have previously been tested from security viewpoints and it can be established that they have no influence on the control of the security-relevant devices.

Advantageously, both control units are components of self-sufficient computers (PCs). It is also possible, however, to integrate the two control units in a single computer that has at least two processors (CPUs) at its disposal, so that in each case one control unit is provided by a processor.

Here, the first control unit and the security-relevant devices are preferably connected to one another by a bus system. Preferably the non-security-relevant devices and the second control unit are connected with one another by an additional bus system, so that the two bus systems preferably are distinct. Therefore current standard bus systems can be used for the other bus system. The more complex bus system of the first control unit is therefore employed only for the connection with the security-relevant devices.

According to a preferred elaboration, an interface unit is provided which on the one hand is connected with the two control units and on the other hand with peripheral devices, and in each case connects one of the two control units with the peripheral devices. The interface unit is preferably controlled by a control line from the first control unit. Further preferable peripheral apparatuses include a display unit and/or an entry device, preferably a keyboard and a mouse. It is also preferable for the display device to take the form of a touch screen, so that entries also can be made by this means.

The aforementioned measures have the advantage that on the one hand the costs for the entire system are reduced and on the other hand operation is clearly simplified, since the peripheral devices required for entering control commands or for monitoring parameters need to be present only once. The operator consequently does not need to keep several display devices in sight. In addition, the control line between the interface unit and the first control unit ensures that the control unit, which controls the important security-relevant devices, also admits the corresponding required functions even in case of an outage or dysfunction of the second control unit and can show the important security-relevant parameters on the touch screen. Altogether, an increase in the security of the system is achieved.

In a preferred elaboration, the second control unit comprises a reception means in order to capture error messages from the first control unit and to display them on one of the peripheral apparatuses. This has the advantage that, also in case of a connection of the second control unit for control of non-security-relevant devices, error reports concerning security-relevant devices are immediately transmitted with the interface unit to the user of the system. This helps to prevent the delay in reporting the depiction of such error reports to the user until the renewed switch-off of the connection from the first control unit to the peripheral apparatuses. This consequently has the advantage that the security of the entire system is further increased.

It is also preferable to connect the two control units with one another by an Ethernet bus (TCP/IP protocol) because this bus system has proved to be reliable and cost-effective.

The first control unit preferably comprises an embedded operating system, preferably embedded Windows NT, which is protected from access from outside. Thus the operating system of the first control unit is an integral part of the unit and thus protected from manipulations. The operator cannot undertake any access to the operating system, such as would be possible for instance with current PCs. This prevents interruptions or defective execution of certain security-relevant functions through intentional or accidental interventions in the operating system.

In a preferred elaboration, the first control unit comprises a testing means that cyclically examines the connection to the interface unit and issues an error report if no connection is in existence. This measure too leads to an increase in security, because the system can inform the user immediately when a depiction or an entry of certain parameters of security-relevant devices is no longer possible because of a defective interface unit.

In a preferred elaboration the first control unit comprises a speech-control unit, for instance in the form of a software module. This measure has the advantage that it becomes possible for the operator to operate the system from inside the sterile area simply and without problems.

In a preferred elaboration, the two control units communicate with one another, and in particular the first control unit checks the second control unit for errors. It is also preferred to provide an interface unit which is controlled by the first control unit and independently of it sends signals on, either from the first or from the second control unit to the common peripheral apparatuses. This feature, as already mentioned, has the advantage of reducing the costs of the system and increasing the visibility of the operation and the operating comfort altogether.

In a preferred elaboration the first control unit in case of a dysfunction of the second control unit will control the interface unit in such a way that the signals of the first control unit are carried on to the peripheral apparatuses. This means that the first control unit ensures that a dysfunction in the second control unit cannot lead to a break in the connection of the first control unit to peripheral apparatuses. In a preferred elaboration the interface unit guides the signals of the first control unit onward to the peripheral apparatuses immediately if a security-relevant function is to be performed. This has the advantage that the important functions are possible between the first control unit and the peripheral apparatuses even when a connection is at first not present. The consequence is an increase in security.

In a preferred elaboration the interface unit, after activating a non-security-relevant function, carries the signals of the second control unit onward to the peripheral apparatuses only if the security-relevant function is completely performed or processed. In other words, the execution of security-relevant functions cannot be interrupted by switching the interface unit. Instead, the execution of the security-relevant function is executed all the way to completion, and only then will the interface unit produce the connection between the second control unit and peripheral apparatuses.

An inventive system for performing medical interventions includes an inventive device for controlling and/or monitoring at least one apparatus during a medical intervention, as well as at least such an apparatus, which on the one hand is connected with the control unit or units, and which on the other hand is connected with at least one intervention element for use in the medical intervention. The intervention element can be, for instance, an insufflation tube, which in turn can be connected with a trocar, through which insufflation gas is conducted into the surgical area, or else for instance a high-voltage surgical instrument.

The object of the invention is also fulfilled through a process having the characteristics of Claim 16, whereby the advantages already described in connection with the inventive device are realized.

Further aspects of the invention can be seen from the following description of a preferred embodiment and from the appended illustration.

It is understood that the aforementioned characteristics and those that remain to be explained hereafter can be used not just in the particular indicated combination but also in other combinations or independently without departing from the framework of the present invention.

DETAILED DESCRIPTION OF THE INVENTION

Figure 1:
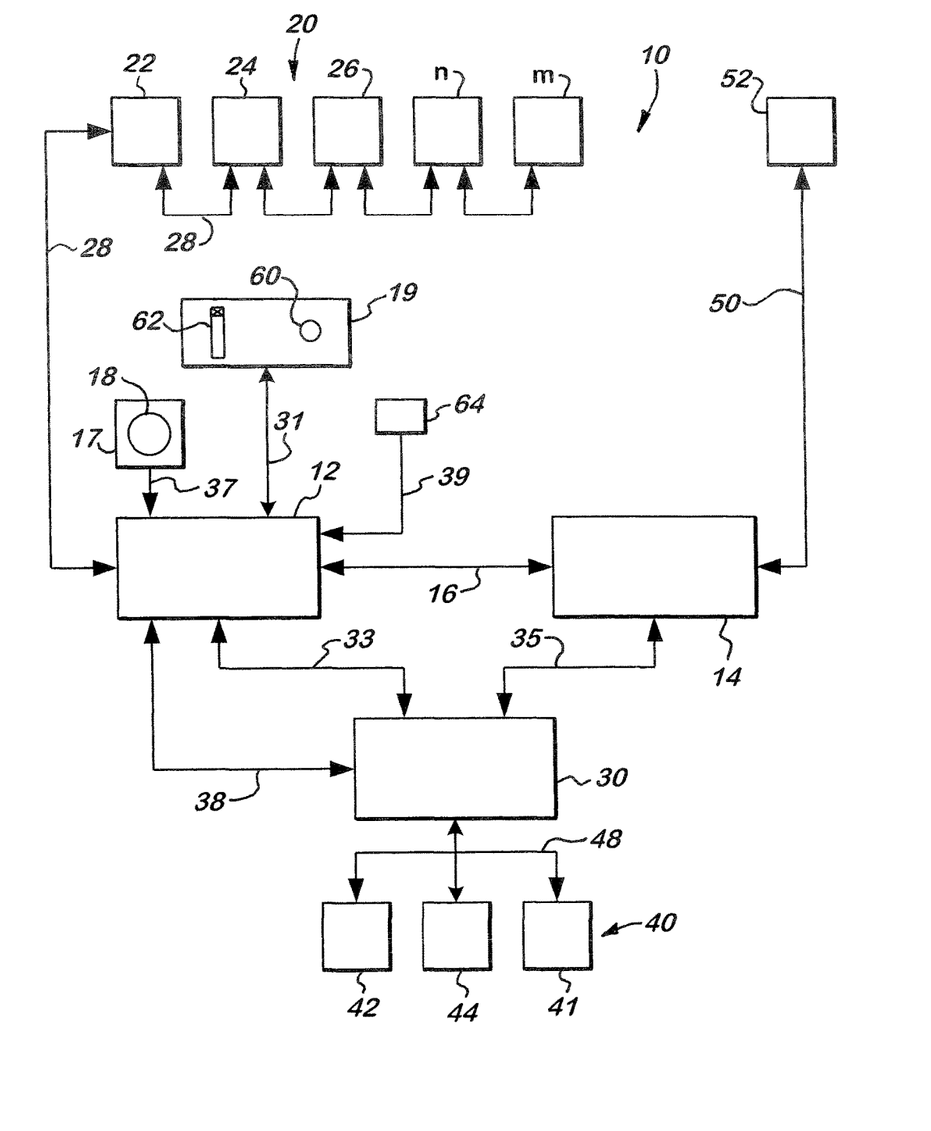
FIG. 1 is a block diagram of a system in accordance with the invention for central control of devices used during an operation.

In FIG. 1 a system for central control of devices that are used during an operation is depicted in the form of a block diagram and is identified with reference numeral 10. The system 10 includes a first control unit 12 and a second control unit 14. The two control units 12, 14 are connected with one another by means of a bus connection 16, for example an Ethernet bus connection, in order to exchange data in the form of reports.

Both control units 12, 14 are configured as medical PCs, and in the first control unit 12 an embedded operating system, preferably an embedded Windows NT operating system, is employed. The second control unit 14 works preferably with a customary Windows operating system or another non-embedded operating system.

The first control unit 12 serves at least for controlling medical devices that perform security-relevant or security-critical functions. In the illustration these security-relevant apparatuses are identified with reference numeral 20. A pump 22, an insufflator 24, and a high-voltage generator 26 are shown in exemplary fashion in the illustration. This exemplary listing of three apparatuses, however, is not to be understood as restrictive, as can be seen in the illustration from additional apparatuses n and m. In addition the first control unit 12 can also be employed for controlling non-security-relevant apparatuses while using correspondingly tested software. Hereafter, however, no further commentary is made on this possibility.

Communication between the first control unit 12 and the security-relevant apparatuses 20 occurs by way of a bus system 28, which makes possible secure transmission of data. With this bus system 28, other criteria concerning error security should be applied such as for example with the aforementioned Ethernet bus 16.

The system 10 also includes a switching unit 30. The switching unit 30 on the inlet side is connected with the control unit 12 and the control unit 14, whereas the illustration depicts in exemplary fashion only one connection line 33, 35 in each case. It is understood that these two connections 33, 35 represent a number of individual connecting lines.

On the outlet side the switching unit 30 is connected with peripheral apparatuses 40, and the figure depicts a touch-sensitive monitor 42 (touch screen), an entry keyboard 44, and a mouse 46 are shown as representative. Peripheral apparatuses 40 are found, for instance, in the direct periphery of a surgeon or of an anesthetist in the operating room so that these peripheral apparatuses 40 must be adjusted to the requirements in this area. The touch screen 42, for instance, is equipped with a sterile covering.

The connection of the peripheral apparatuses 40 with the switching unit 30 is managed by way of corresponding lines 48, and here too for the sake of simplicity only one line in each case is depicted to represent a number of connecting lines.

The switching unit 30 now has the task of connecting the individual peripheral apparatuses 42 through 46 with one of the two control units 12, 14, so that the entry or depiction of data becomes possible.

Control of the switching unit 30 is taken over by the first control unit 12, and corresponding control signals can be conveyed to the switching unit 30 by a control line 38.

The control unit 12 is connected with a fingerprint recognition apparatus 64 by means of a connecting line 39.

Before modifications to the configuration or parameter values can be made by the attending physician, the physician must first identify himself by, for instance, placing his right index fingertip on the fingerprint recognition apparatus 62. The fingerprint recognition apparatus scans the fingerprint and compares it with fingerprints on file. If the scanned fingerprint corresponds with a fingerprint on file, modifications in the apparatus configurations and parameter values for control of security-relevant devices can be triggered for the control of security-relevant devices by the control unit 12.

The control unit 12 is connected by a connecting line 37 with a data reader 17, for instance a CD ROM drive. Located in the data reader apparatus 17 is a data carrier 18, for instance a compact disc, on which an OP atlas with a database of parameter settings for control of security-relevant devices is found.

The information on the data carrier 18 can be read by the control unit 12 by way of the connecting line 37 and can be represented on the display device 42. The attending physician can make a choice of parameter presettings for control of the security-relevant devices 22, 24, and 26 and depending on the case can adapt the parameter presettings to the requirements of the medical intervention by entries on the touch screen 42 or by way of the entry keyboard 44 or the mouse 46. After selecting the parameter settings for control of security-relevant devices, which are displayed on the display device 42, the attending physician must confirm his selection by actuating the switch 62 of the confirming element 19. Only the motion of the switch 62 causes a signal to be transmitted by the connecting line 31 onto the control unit 12, which signal initiates the transmission of the parameter settings from the control unit 12 by way of the bus system 28 onto the security-relevant apparatuses 22, 24, and 26. The transmitted parameter values are incorporated by the apparatuses 22, 24, and 26 and the condition of the apparatuses is adjusted accordingly.

The control light 60 by its illumination indicates whether the parameter values depicted on the display device 42 have been transmitted to the security-relevant apparatuses. If the control light 60 is not illuminated, it signals to the user that no selection of parameter settings has yet been made, or that no selection has been made that is valid according to a plausibility test executed by the control unit 12.

The second control unit 14 is connected, galvanically insulated, by means of an optical bus 50 with apparatuses 52, which perform non-security-relevant functions. They include for instance a telephone remote operation, the room lighting, and so on. The control of these non-security-relevant apparatuses is thus performed by the second control unit 14.

As already mentioned, the first control unit 12 is equipped with an embedded operating system. This is intended to ensure that interventions or manipulations are not possible on the system from outside. The first control unit 12 instead is configured as a closed system on which essentially only those tasks are conducted which are required for the control of the security-relevant apparatuses 20. If aptness has been correspondingly tested, in addition tasks can take place that serve to control the non-security-relevant apparatuses 52.

The second control unit 14, on the other hand, is configured as a customary medical PC. Contrary to the first control unit 12, on the second control unit 14 no tasks can run that serve to control security-relevant apparatuses.

The two control units 12, 14 supply data over the corresponding lines 33, 35 to the switching unit 30, and depending on the condition of the switching unit only the data of one of the two control units are depicted on the touch screen 42. Data entry also occurs then only in this control unit. If the operator would like to select, for instance, functions of the other group of apparatuses, then he can do so by entering a corresponding command which is received either directly by the first control unit 12 or indirectly through the control unit 14 and the bus 16 by the first control unit 12. Unit 12 thereupon emits a corresponding control signal over the control line 38, leading to a switching in the switching unit 30. Then, the corresponding data, selection menus, and so on of the selected group of apparatuses are depicted on the touch screen 42.

In case of a connection of the second control unit 14 with the peripheral apparatuses 40, it is necessary, however, that every single error report that concerns security-relevant apparatuses 20 is informed immediately to the operator through the touch screen 42 independently of the switching condition of the switching unit 30. In the second control unit 14, for this purpose, a task is run that constantly runs tests for defective reports on the reports delivered through the bus 16 by the first control unit 12. Upon detecting a defective report, the second control unit 14 ensures that a window is opened on the touch screen in which this defective report is depicted.

An additional task of the first control unit 12 consists in verifying the presence of the switching unit 30. If the switching unit 30, for instance, is offline and therefore can no longer by recognized by the first control unit 12, it must immediately submit a failure report. This failure report is intended to signal to the operator that the correct depiction and the entry of data are no longer ensured by the peripheral apparatuses 40.

It is further necessary that the first control unit 12 tests the second control unit 14 and, in case of defect, immediately moves the switching unit 30 into that switching position in which the first control unit 12 is connected with the peripheral apparatuses 40.

Among security aspects, in addition, it is essential that in case of the entry of a command for switching the peripheral apparatuses 40 to the second control unit 14, at first all functions of security-relevant apparatuses 20 that have not yet been completed are conducted with a corresponding depiction of the parameters. This is intended to ensure that the execution of these security-relevant functions is not ended prematurely. In the contrary case, however, the peripheral apparatuses 40 are connected immediately with the first control unit 12, so that security-relevant functions can be conducted immediately without any delays.

What is claimed is:

1. A device for controlling and/or monitoring at least one apparatus during a medical intervention, including:
    a first control unit for controlling and/or monitoring at least one security relevant apparatus,
    a second control unit for controlling non-security relevant apparatuses, said second control unit in communication with said first control unit,
    an interface unit, said interface unit being connected to the first and second control units and to the non-security relevant apparatuses,
    the non-security relevant apparatuses including at least one display unit for displaying data, and
    a database accessible by said first control unit, said database comprising data parameter values to be entered on the at least one security relevant apparatus during a predetermined intervention,
    wherein the parameter values are predetermined independently of a user, at least in part, wherein the parameter values is called up by the user for display on the display unit, wherein said first control unit comprises monitoring measures for testing the plausibility of the parameter values before releasing the parameter values, and wherein a confirming element is provided for receiving confirmation from the user, through whose actuation the released parameter values for the at least one security relevant apparatus are incorporated;
    wherein said monitoring measures are also configured to detect errors in the at least one security relevant apparatus and to generate error messages regarding the at least one security relevant apparatus, wherein said second control unit includes a reception means for capturing the error messages to display on the display unit;
    wherein said monitoring measures are further configured to detect errors in the said second control unit, wherein said first control unit is configured to control the non-security relevant apparatuses upon detecting an error of said second control unit via the interface unit,
    wherein said at least one security relevant apparatus is medical device, and
    wherein said non-security relevant apparatuses are non-medical devices.

2. The device as in claim 1, wherein the user, after the display of the user-independently predetermined parameter values, to modify parameter values for use in one or more interventions, and wherein after confirmation of the confirming element the modified parameter values for the at least one security relevant apparatus are incorporated.

3. The device as in claim 2, wherein the confirming element is configured as a switching surface on the operating surface of a touch screen and the touch screen serves simultaneously to display the parameter values and for entry of modified parameter values.

4. The device as in claim 1, wherein the data specific to the intervention also include predetermined data on the apparatus configuration that is to be used in the predetermined intervention.

5. The device as in claim 4, wherein the predetermined data on the apparatus configuration include type and number of the apparatuses to be used in the predetermined intervention.

6. The device as in claim 1, wherein the predetermined or modified parameter values, after actuation of the confirming element, are transmitted to the apparatus or apparatuses that correspond to the predetermined apparatus configuration.

7. The device as in claim 1, wherein the predetermined or modified parameter values are transmitted before actuation of the confirming element to the apparatus or apparatuses that correspond to the predetermined apparatus configuration, and wherein after actuation of the confirming element an actuation signal is transmitted for taking over the parameter values.

8. The device as in claim 1, wherein the actuation of the confirming element also triggers processes to documentation and/or administrative processes.

9. The device as in claim 1, wherein the confirming element is configured as a switch and a control element is provided that issues a signal upon actuation of the confirming element.

10. The device as in claim 9, wherein said signal is a control lamp that lights up or an acoustical element that produces a control tone.

11. The device as in claim 1, wherein the data specific to the intervention are specific to the situation and/or patient or can be adapted specifically to the situation and/or patient.

12. The device as in claim 1, wherein the device includes storage capacity in which the data specific to the intervention can be stored.

13. The device as in claim 1 further including an authentication means for authenticating a user, wherein said first control unit is enabled to receive confirmation from the user after the authentication.

14. The device as in claim 13, wherein said authentication means is provided by verifying a key, a password, barcode, magnetic card, a chip, or biometrical data.

15. The device as in claim 13, wherein said authentication means is provided by verifying fingerprint or interocular distance of the user.

16. The device as in claim 1, wherein said first control unit comprises a speech control unit.

17. A process for controlling and/or monitoring at least one apparatus in a medical intervention, including the following steps:

providing a first control unit for controlling at least one security relevant apparatus, providing a second control unit for controlling non-security relevant apparatuses, said second control unit in communication with said first control unit, providing an interface unit, said interface unit being connected to the first and second control units and to the non-security relevant apparatuses, providing access to data specific to the intervention, which include data predetermined independently of a user on the parameter values to be entered on the at least one security relevant apparatus during a predetermined intervention, retrieving the data specific to the intervention upon demand by the user, display of the data specific to the intervention on a display unity, testing the plausibility of the data specific to the intervention, transmitting the data specific to the intervention to the at least one security relevant apparatus through said first control unit after actuation of a confirming element by the user, adjusting the condition of the at least one apparatus according to the transmitted data specific to the intervention;

detecting errors in said second control unit through said first control unit; and transmitting signals from said first control unit to the non-security relevant apparatuses upon detecting an error of said second control unit via the interface unit, wherein said at least one security relevant apparatus is medical device, and wherein said non-security relevant apparatuses are non-medical devices.

18. The process as in claim 17, wherein after display of the data specific to the intervention, the user can modify the parameter values, and after actuation of the confirming element by the user the modified parameter values for the at least one apparatus are incorporated.

* * * * *